(12) United States Patent
Feng

(10) Patent No.: US 9,995,727 B2
(45) Date of Patent: Jun. 12, 2018

(54) MECHANICAL PROPERTY TESTER AND TESTING METHOD OF BIOLOGICAL SOFT TISSUE

(71) Applicant: Soochow University, Suzhou, Jiangsu (CN)

(72) Inventor: Yuan Feng, Jiangsu (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days. days.

(21) Appl. No.: 15/308,168

(22) PCT Filed: Nov. 3, 2015

(86) PCT No.: PCT/CN2015/093628
§ 371 (c)(1),
(2) Date: Nov. 1, 2016

(87) PCT Pub. No.: WO2017/070975
PCT Pub. Date: May 4, 2017

(65) Prior Publication Data
US 2017/0269057 A1    Sep. 21, 2017

(30) Foreign Application Priority Data

Oct. 26, 2015  (CN) .......................... 2015 1 0701187

(51) Int. Cl.
*G01N 3/08* (2006.01)
*G01N 33/483* (2006.01)
(Continued)

(52) U.S. Cl.
CPC ........... *G01N 33/4833* (2013.01); *G01N 3/04* (2013.01); *G01N 3/066* (2013.01); *G01N 3/08* (2013.01)

(58) Field of Classification Search
CPC ... A61B 5/4884; A61B 5/0048; A61B 5/0053; G01N 3/24; G01N 2203/0254;
(Continued)

(56) References Cited

U.S. PATENT DOCUMENTS 4,901,581 A * 2/1990 Fain ....................... G01L 5/0033
73/159
4,947,851 A * 8/1990 Sarvazyan ........... A61B 5/0051
600/438
(Continued)

FOREIGN PATENT DOCUMENTS

CN        102252786 A     11/2011
CN        202057562 U     11/2011
(Continued)

*Primary Examiner* — Harshad R Patel
*Assistant Examiner* — Tran M Tran
(74) *Attorney, Agent, or Firm* — SZDC Law P.C.

(57) ABSTRACT

A mechanical property tester includes a base, a fixture for fixing the biological soft tissue, a transverse force applying device for applying a transverse force, a vertical force applying device for applying a vertical force, a longitudinal pulling force detector for detecting a longitudinal force, a displacement detecting unit for detecting the displacement of the fixture, an acquisition device and a computer. The transverse force applying device includes a transverse pulling force detector for detecting the transverse force. The vertical force applying device includes a vertical pulling force detector for detecting the vertical force. The acquisition device is used for collecting the longitudinal force, transverse force, vertical force and the displacement. The computer is connected with the acquisition device to analyze the longitudinal force, transverse force, vertical force, and the displacement.

8 Claims, 3 Drawing Sheets

(51) Int. Cl.
  *G01N 3/04* (2006.01)
  *G01N 3/06* (2006.01)

(58) Field of Classification Search
  CPC ... G01N 2203/0025; G01N 2203/0256; G01N 2203/0282; G01N 2203/0278
  See application file for complete search history.

(56) References Cited

U.S. PATENT DOCUMENTS

| | | | | |
|---|---|---|---|---|
| 5,054,502 A * | 10/1991 | Courage | ............... | A61B 5/441 600/476 |
| 5,107,837 A * | 4/1992 | Ophir | ................ | A61B 5/441 600/437 |
| 5,115,808 A * | 5/1992 | Popovic | ............... | A61B 5/0051 600/438 |
| 5,448,918 A * | 9/1995 | Tucchio | ................ | G01N 3/04 73/818 |
| 5,850,043 A * | 12/1998 | Robinett | ............ | G01M 5/0025 73/786 |
| 6,078,387 A * | 6/2000 | Sykes | ................. | G01R 1/06705 356/213 |
| 6,247,370 B1 * | 6/2001 | Ramaswamy | .......... | G01N 3/08 73/798 |
| 6,332,364 B1 * | 12/2001 | Buschmann | ............. | G01N 3/08 73/788 |
| 6,487,902 B1 * | 12/2002 | Ghosh | ................... | G01L 5/045 73/159 |
| 6,619,423 B2 * | 9/2003 | Courage | .............. | A61B 5/0051 181/101 |
| 6,860,156 B1 * | 3/2005 | Cavallaro | ................ | G01N 3/08 73/813 |
| 7,051,600 B1 * | 5/2006 | Cavallaro | ................ | G01N 3/08 73/862.041 |
| 7,204,160 B1 * | 4/2007 | Sadegh | .................... | G01N 3/10 73/862.041 |
| 7,435,232 B2 * | 10/2008 | Liebschner | .......... | A61B 5/4504 128/920 |
| 7,472,602 B1 * | 1/2009 | Feng | ......................... | G01N 3/10 73/150 A |
| 7,509,882 B2 * | 3/2009 | Monteiro | ................. | G01N 3/08 73/862.046 |
| 7,533,577 B1 * | 5/2009 | Feng | ......................... | G01N 3/10 73/150 A |
| 7,553,662 B2 * | 6/2009 | El Haj | ................... | C12M 25/14 435/325 |
| 7,712,379 B2 * | 5/2010 | Abu-Farha | ............... | G01N 3/04 73/856 |
| 7,762,146 B2 * | 7/2010 | Brodland | ................. | G01N 3/04 73/826 |
| 7,772,000 B2 * | 8/2010 | Hauselmann | ........... | A61L 27/28 435/283.1 |
| 8,027,819 B2 * | 9/2011 | Yoshida | .................. | B23K 11/11 219/109 |
| 8,061,214 B2 * | 11/2011 | Liggett | .................... | G01N 3/08 73/788 |
| 8,082,802 B1 * | 12/2011 | Sadegh | .................... | G01N 3/08 73/760 |
| 8,175,689 B2 * | 5/2012 | Hunter-Jones | ......... | A61B 5/442 356/244 |
| 8,375,804 B2 * | 2/2013 | Su | ............................ | G01N 3/24 73/150 A |
| 8,671,771 B2 * | 3/2014 | Hanabusa | ................ | G01N 3/04 73/826 |
| 8,763,472 B2 * | 7/2014 | Abelev | ................... | G01N 11/14 73/841 |
| 8,950,268 B2 * | 2/2015 | Ota | ........................... | G01N 3/12 73/788 |
| 8,978,480 B2 * | 3/2015 | Michopoulos | ........... | G01N 3/08 73/857 |
| 9,032,817 B2 * | 5/2015 | Berme | ..................... | G01L 5/161 73/862.045 |
| 9,400,238 B2 * | 7/2016 | Bin | ........................... | G01N 3/24 |
| 9,423,329 B2 * | 8/2016 | Takeda | .................... | G01N 3/08 |
| 9,482,604 B2 * | 11/2016 | Campbell | ............... | G01N 3/08 |
| 9,746,401 B2 * | 8/2017 | Kanade | ................... | G01N 3/02 |
| 2008/0200842 A1 * | 8/2008 | Lim | ..................... | A61B 5/0053 600/587 |
| 2011/0319792 A1 * | 12/2011 | Lim | ..................... | A61B 5/0053 600/595 |
| 2014/0100138 A1 * | 4/2014 | Botvinick | ........ | G01N 33/54373 506/10 |
| 2016/0091375 A1 * | 3/2016 | Belzacq | .................... | G01L 5/00 73/804 |
| 2016/0258837 A1 * | 9/2016 | Rastegar | ................ | G01M 7/08 |
| 2017/0059557 A1 * | 3/2017 | Botvinick | ........ | G01N 33/54373 |
| 2017/0268970 A1 * | 9/2017 | Heinlein | ................ | G01N 3/068 |

FOREIGN PATENT DOCUMENTS

| | | |
|---|---|---|
| CN | 103604937 A | 2/2014 |
| CN | 104977211 A | 10/2015 |
| CN | 205192870 U | 4/2016 |
| WO | 2007004993 A1 | 1/2007 |
| WO | 2014090298 A1 | 6/2014 |

* cited by examiner

MECHANICAL PROPERTY TESTER AND TESTING METHOD OF BIOLOGICAL SOFT TISSUE

This application is a national stage application of PCT/CN2015/093628, filed on Nov. 3, 2015, which claims the benefits of Chinese Patent Application Ser. No. 201510701187.2, field Oct. 26, 2015 and entitled "Mechanical Property Tester and Testing Method of Biological Soft Tissue", the entire contents of which are incorporated herein by reference.

FIELD OF THE INVENTION

The present invention relates to the field of tissue engineering and biomedical engineering, and more particularly to a mechanical property tester and testing method of biological soft tissue.

DESCRIPTION OF THE RELATED ART

Measurement of mechanical properties of soft biological tissue is a crucial step in the research and development of medical devices and tissue engineering. Soft biological tissues have various mechanical properties due to different structures and constituents. Current methods of measuring mechanical properties of soft biological tissues mainly include compression test, tension test, and shear test. However, the existing instruments for shear test have the following disadvantages: the shear tester is mainly used for characterizing isotropic materials, the shear direction is limited, and material response in complex shear mode could not be tested.

SUMMARY OF THE INVENTION

An object of the present invention is to provide a mechanical property tester of biological soft tissue, and the mechanical property tester can achieve the shear test of biological soft tissue, and test the material response in complex shear mode.

For the above technical purpose, the invention utilizes the following technical solutions.

In an aspect, the invention provides a mechanical property tester of biological soft tissue, the mechanical property tester comprises:

a base;

a fixture disposed on the base for fixing the biological soft tissue;

a transverse force applying device connected with the fixture for applying a transverse force on the fixture, the transverse force applying device comprising a transverse pulling force detector for detecting the transverse force applied on the fixture;

a vertical force applying device connected with the fixture for applying a vertical force on the fixture, the vertical force applying device comprising a vertical pulling force detector for detecting the vertical force applied on the fixture;

a longitudinal pulling force detector for holding the fixture and detecting a longitudinal force applied on the fixture, a displacement detecting unit disposed on the base for detecting the displacement of the fixture, an acquisition device for collecting the longitudinal force, the transverse force, the vertical force and the displacement; and a computer connected with the acquisition device via signals, for analyzing the longitudinal force, the transverse force, the vertical force and the displacement.

Preferably, the displacement detecting unit comprises a Y-axis displacement detector for detecting the displacement of the fixture in a longitudinal direction, an X-axis displacement detector for detecting the displacement of the fixture in a transverse direction, and a Z-axis displacement detector for detecting the displacement of the fixture in a vertical direction.

Preferably, a fixing frame is provided on the base for fixing the Y-axis displacement detector which is located above the fixture, the fixing frame comprises a fixing rod disposed vertically relative to the base, a mounting rod disposed vertically relative to the fixing rod and a fastener for fixing the mounting rod on the fixing rod, an elongated waist hole extending along the mounting rod is opened on the mounting rod, and the fastener extends through the elongated waist hole.

Preferably, the longitudinal pulling force detector comprises a plurality of clamping elements for clamping the fixtures and multiple longitudinal pressure sub-detectors disposed correspondingly to the clamping elements, each of the longitudinal pressure sub-detectors detects the longitudinal force of the fixture at the position of the corresponding clamping element.

More preferably, there are four clamping elements, the fixture is quadrangular, and the four clamping elements hold the four corners of the fixture respectively.

Still more preferably, each clamping element comprises an upper clamping board and a lower clamping board disposed oppositely and a connecting board for connecting the upper and lower clamping boards, a clamping chamber is enclosed by the upper clamping board, the lower clamping board and the connecting board. The fixture is C-shaped.

Preferably, the transverse force applying device also comprises a transverse traction wire for connecting the transverse pulling force detector with the fixture, the vertical force applying device also comprises a vertical traction wire for connecting the vertical pulling force detector with the fixture.

More preferably, the transverse force applying device also comprises a transverse driving device for driving the transverse traction wire, one end of the transverse pulling force detector is connected with the transverse traction wire, and the other end is connected with the transverse driving device, the vertical force applying device also comprises a vertical driving device for driving the vertical traction wire, one end of the vertical pulling force detector is connected with the vertical traction wire, and the other end is connected with the vertical driving device.

Preferably, the base is provided with a mounting base, and a first sliding base and a second sliding base which are fixed on the mounting base, the transverse pulling force detector is provided on the first sliding base, the vertical pulling force is provided on the second sliding base. The mounting base comprises a fixture mounting part for fixing the fixture, a first extension plate and a second extension plate extending outwardly from the two adjacent lateral surfaces of the mounting part. The first extension plate is provided with a first rail extending along the extension direction of the transverse traction wire and cooperated with the first sliding base. The second extension plate is provided with a second rail extending along the extension direction of the vertical traction wire and cooperated with the second sliding base.

In another aspect, the invention provides a mechanical property testing method of biological soft tissue, for use in a mechanical property tester of biological soft tissue. The mechanical property tester comprises a fixture for fixing the biological soft tissue, a transverse force applying device for applying a transverse force on the fixture, a vertical force applying device for applying a vertical force on the fixture, a longitudinal pulling force detector connected with the fixture for detecting a longitudinal force applied on the fixture, a displacement detecting unit for detecting the displacement of the fixture, an acquisition device and a computer. The mechanical property testing method comprises the steps of:

fixing the biological soft tissue on the fixture of the mechanical property tester of biological soft tissue;

applying a force on the fixture by the vertical force applying device and transverse force applying device, such that the fixture is displaced and the biological soft tissue is deformed;

detecting the longitudinal force, the transverse force, the vertical force and the displacement by the longitudinal pulling force detector, the transverse force applying device, the vertical force applying device and the displacement detecting unit respectively;

collecting the longitudinal force, the transverse force, the vertical force and the displacement amount by the acquisition device; and analyzing the longitudinal force, the transverse force, the vertical force and of the displacement amount collected by the acquisition device, to obtain the mechanical property of the biological soft tissue.

Due to the above technical solutions, as compared with the prior art the present invention has the following advantages: in the mechanical property tester of biological soft tissue of the present invention, a fixture is provided for fixing the biological soft tissue, a transverse force applying device is provided for applying a force on the fixture, a vertical force applying device is provided such that shear deformation is caused in the biological soft tissue. And, the longitudinal force, the transverse force, the vertical force, and the amount of displacement are detected by the longitudinal pulling force detector, the transverse pulling force detector, the vertical pulling force detector and the displacement detecting unit respectively and analyzed. Thus, by means of the mechanical property tester and testing method of the invention, the shear test can be achieved in biological soft tissue, and the material response can be measured in complex shear mode.

DESCRIPTION OF THE PREFERRED EMBODIMENTS

The invention will be further illustrated in more detail with reference to accompanying drawings. It is noted that, the following embodiments are intended for purposes of illustration only and are not intended to limit the scope of the invention.

Figure 1:
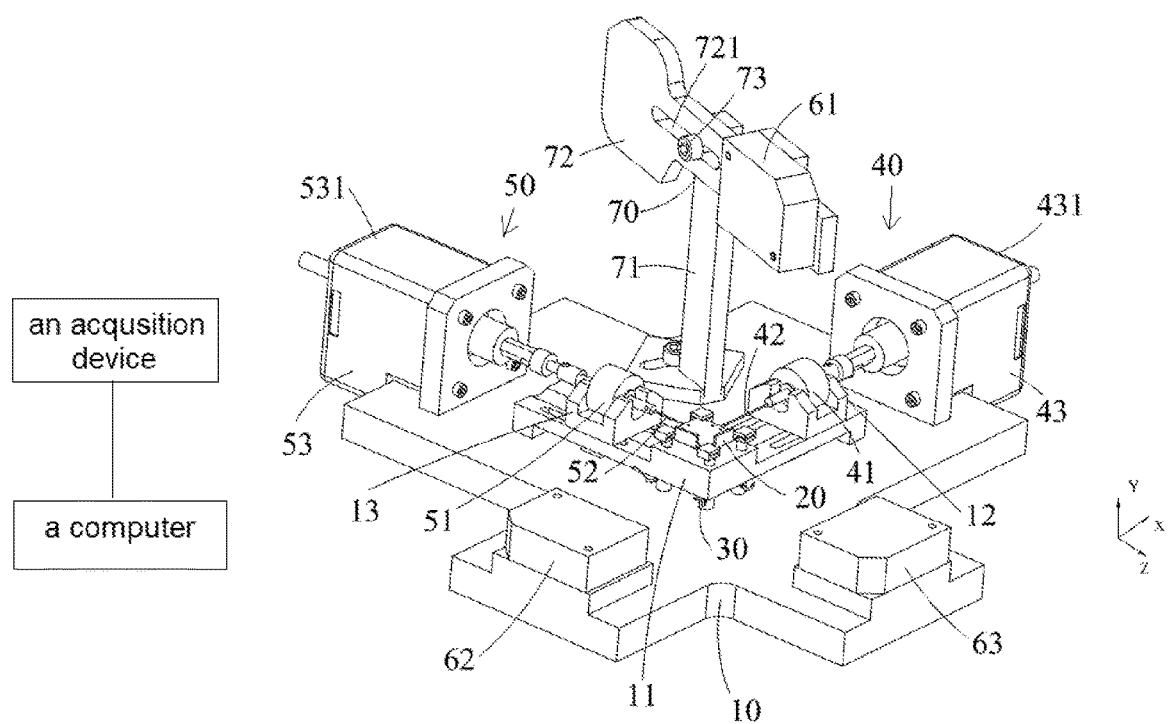
FIG. 1 is a schematic view of a mechanical property tester of biological soft tissue according to the invention.
Figure 2:
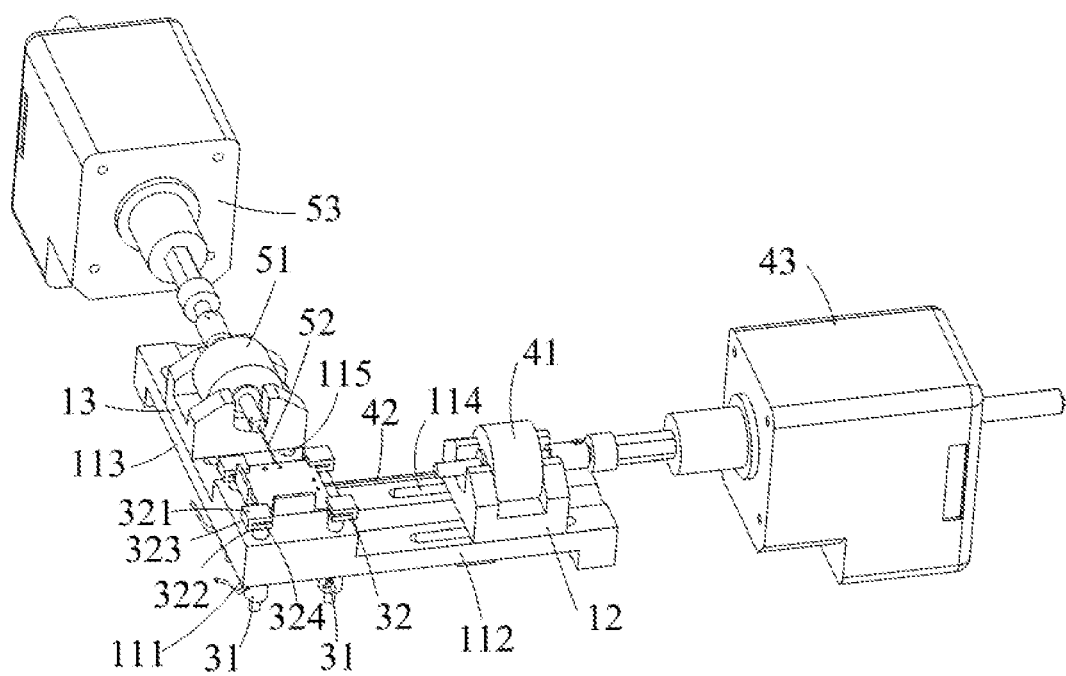
FIG. 2 is a partial view of the mechanical property tester of biological soft tissue according to the invention.
Figure 3:
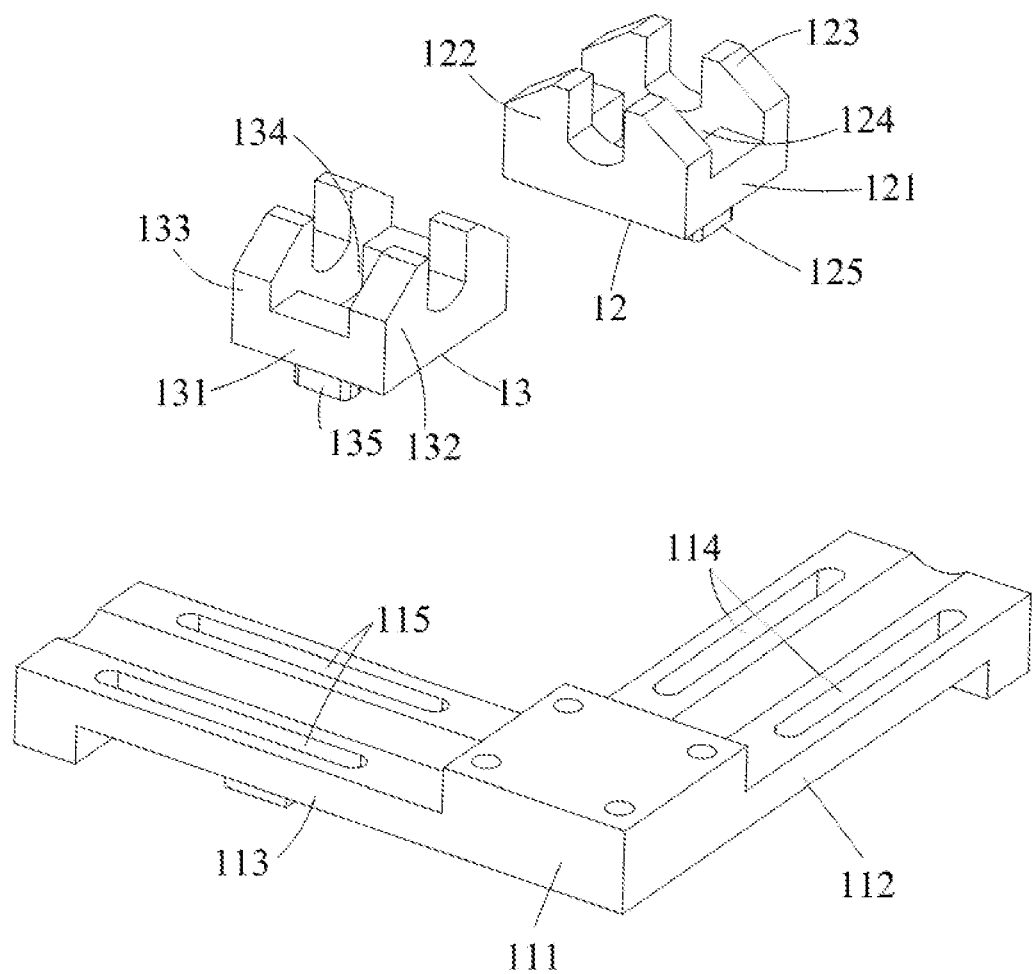
FIG. 3 is an exploded view of the mounting base, the first sliding base and the second sliding base of the FIG. 2.

Referring to FIG. 1 to FIG. 3, a mechanical property tester of biological soft tissue is disclosed in a preferred embodiment of the invention. The mechanical property tester of biological soft tissue is used to test the mechanical properties of biological soft tissues. The mechanical property tester of biological soft tissue comprises a base 10, a fixture 20 disposed on the base 10 for fixing the biological soft tissue, a transverse force applying device 40 connected with the fixture 20 for applying a transverse force onto the fixture 20, a vertical force applying device 50 connected with the fixture 20 for applying a vertical force onto the fixture 20, a longitudinal pulling force detector 30 for holding the fixture 20 and detecting a longitudinal force applied on the fixture 20, a displacement detecting unit disposed on the base 10 for detecting the displacement amount of the fixture 20, an acquisition device (not shown) and a computer.

The transverse force applying device 40 includes a transverse pulling force detector 41 for detecting the transverse force applied on the fixture 20, a transverse traction wire 42 for connecting with the transverse pulling force detector 41 with the fixture 20, and a transverse driving device 43 for driving the transverse traction wire 42. The transverse force detected by the transverse pulling force detector 41 is a transverse traction force. The transverse traction wire 42, the transverse pulling force detector 41 and the transverse driving device 43 are connected with each other in sequence along the extension direction of the transverse traction wire 42. One end of the transverse pulling force detector 41 is connected to the transverse traction wire 42, and the other end is connected to the transverse driving device 43. The transverse driving device 43 drives the transverse traction wire 42 and the transverse pulling force detector 41 to move along the extension direction of the transverse traction wire 42. In this embodiment, the transverse driving device 43 is a motor, which comprises a first shell 431 mounted on the base 10. The vertical force applying device 50 includes a vertical pulling force detector 51 for detecting the vertical force applied on the fixture 20, a vertical traction wire 52 for connecting the vertical pulling force detector 51 and the fixture 20, and a vertical driving device 53 for driving the vertical traction wire 52. The vertical force detected by the vertical pulling force detector 51 is a vertical traction force. The vertical pull wire 52, the vertical pulling force detector 51, and the vertical driving device 53 are connected with each other in sequence along the extension direction of the vertical traction wire 52. One end of the vertical pulling force detector 51 is connected to the vertical traction wire 52, and the other end is connected to the vertical driving device 53. The vertical driving device 53 drives the vertical traction wire 52 and the vertical pulling force detector 51 move along the extension direction of the vertical traction wire 52. In this embodiment, the vertical driving device 53 is a motor, which comprises a second shell 531 mounted on the base 10. The transverse traction wire 42 and the vertical traction wire 52 are fixed on the two adjacent lateral sides of the quadrangular fixture 20 respectively.

The longitudinal pulling force detector 30 comprises a plurality of clamping elements 32 for clamping the fixture 20, and multiple longitudinal pressure sub-detectors 31 disposed correspondingly to the clamping elements 32, each of the longitudinal pressure sub-detectors 31 detects the longitudinal force of the fixture at the position of the corresponding clamping element 32. Each of the clamping elements 32 comprises an upper clamping board 321 and a lower clamping board 322 disposed oppositely, and a connecting board 323 for connecting the upper and lower clamping boards. A clamping chamber 324 is enclosed by the upper clamping board 321, the lower clamping board 322 and the connecting board 323. The fixture 20 is C-shaped. In this embodiment, there are four clamping elements 32, the fixture 20 is quadrangular and made of transparent organic glass. The four clamping elements 32 clamp the four corners of the fixture 20 respectively. The longitudinal pressure sub-detector 31 is located below the fixture 20.

The base 10 is provide with a mounting base 11, and a first sliding base 12 and a second sliding base 13 which are fixed on the mounting base 11. The mounting base 11 comprises a mounting part 111 for fixing the fixture, a first extension plate 112 and a second extension plate 113 extending outwardly from the two adjacent lateral surfaces of the mounting part 111. The mounting part 111 is configured as a cube. The upper surface of the mounting part 111 is above the upper surfaces of the first extension plate 112 and the second extension board 113 in the longitudinal direction. The first extension board 112 is provided with a first rail 114 which extends along the extension direction of the transverse traction wire 42 and is cooperated with the first sliding base 12. The second extension board 113 is provided with a second rail 115 which extends along the extension direction of the vertical traction wire 52 and is cooperated with the second sliding base 13. The first rail 114 and the second rail 115 are grooves opened on the first extension board 112 and the second extension board 113 respectively. The transverse pulling force detector 41 is disposed on the first sliding base 12, and the vertical pulling force detector 51 is disposed on the second sliding base 13. The first sliding base 12 has a first bottom wall 121, a first front wall 122 and a first rear wall 123 extending upwardly from the front and rear surfaces of the first bottom wall 121. A first mounting groove 124 is enclosed by the first bottom wall 121, the first front wall 122 and the first rear wall 123. The transverse pulling force detector 41 is fixed in the first mounting groove 124. A first sliding block 125 is protruded downwardly from the first bottom wall 121 of the first sliding base 12, and is inserted into the first rail 114. The second sliding base 13 is driven by the vertical driving device 53 to move along the extension direction of the vertical traction wire 52 relative to the base 10. The second sliding base 13 has a second bottom wall 131, a second front wall 132 and a second rear wall 133 extending upwardly from the front and rear surfaces of the second bottom ball 131. A second mounting groove 134 is enclosed by the second bottom wall 131, the second front wall 132 and the second rear wall 133. The vertical pulling force detector 51 is fixed in the second mounting groove 134. A second sliding block 134 is protruded downwardly from the second bottom wall 131 of the second sliding base 13, and is inserted into the second rail 115. The first sliding base 12 is cooperated with the first rail 114, the second sliding base 13 is cooperated with the second rail 115, the transverse pulling force detector 41 is fixed in the first sliding base 12, and the vertical pulling force detector 51 is fixed in the second sliding base 13, such that the transverse pulling force detector 41 and the vertical pulling force detector 51 can be moved smoothly. Most importantly, the sinking of the transverse pulling force detector 41 and the vertical pulling force detector 51 due to their own weight can be prevented, thereby avoiding the inaccuracy of the detected transverse force and vertical force.

The displacement detecting unit comprises a Y-axis displacement detector 61 for detecting the displacement amount of the fixture 20 in a longitudinal direction, an X-axis displacement detector 62 for detecting the displacement amount of the fixture 20 in a transverse direction, and a Z-axis displacement detector 63 for detecting the displacement amount of the fixture 20 in a vertical direction. The Y-axis displacement detector 61 is located above the fixture 20, and the Y-axis displacement detector 61 and the longitudinal pulling force detector 30 are disposed oppositely on the upper and lower sides of the mounting part 111 respectively. A fixing frame 70 is disposed on the base 10 for fixing the Y-axis displacement detector 61. In this embodiment, the fixing frame 70 comprises a fixing rod 71 disposed vertically relative to the base 10, a mounting rod 72 disposed vertically relative to the fixing rod 71, and a fastener 73 for fixing the mounting rod 72 on the fixing rod 71. An elongated waist hole 721 extending along the mounting rod 72 is opened on the mounting rod 72, and the fastener 73 is extended through the elongated waist hole 721, such that the position of the Y-axis displacement detector 61 in the horizontal direction can be adjusted by means of the cooperation of the elongated waist hole 721 with the fastener 73. Certainly, the fixing frame 70 for fixing the Y-axis displacement detector 61 can be configured as other structures, such as a lifting base. The movement of Y-axis displacement detector 61 in the horizontal direction also can be achieved by other means, for example, by means of a guide rail assembly. The X-axis displacement detector 62 and the transverse force applying device 40 are disposed oppositely at two sides of the mounting base 11. The Z-axis displacement detector 63 and the vertical force applying device 50 are disposed oppositely at two sides of the mounting base 11.

The acquisition device collects the longitudinal force, the transverse force, the vertical force and the amount of displacement. The computer is connected with the acquisition device, and analyzes the longitudinal force, the transverse force, the vertical force and the amount of displacement to obtain the mechanical property of biological soft tissue.

The mechanical property testing method of biological soft tissue of the present invention is applicable to the above mechanical property tester of biological soft tissue, in other words, the mechanical property testing method of biological soft tissue refers to the working method of the above mechanical property tester of biological soft tissue. The mechanical property tester of the biological soft tissue will not be described in more detail here, because it has been described above. The mechanical property testing method of biological soft tissue comprises the following steps:

S1: the biological soft tissue is fixed on the fixture 20 of the mechanical property tester of biological soft tissue, and the fixture 20 is clamped by the clamping element 32.

S2: the transverse force applying device 40 and the vertical force applying device 50 are actuated to apply a force to the fixture 20 at two adjacent edges thereof, such that the fixture 20 is displaced. Because the biological soft tissue is fixed on the fixture 20, shear deformation is caused in the biological soft tissue during the displacement of the fixture 20. Specifically, The transverse driving device 43 of the transverse force applying device 40 and the vertical driving device 53 of the vertical force applying device 50 are activated to apply a force far away from the fixture 20 on the transverse traction wire 42 and the vertical traction wire 43 respectively, such that the fixture 20 is stretched outwardly by the transverse traction wire 42 and the vertical traction wire 52.

S3: when the fixture 20 is displaced, the longitudinal pressure sub-detector 31 of the longitudinal pulling force detector 30, the transverse pulling force detector 41 of the transverse force applying device 40, and the vertical pulling force detector 51 of the vertical force applying device 50 and the displacement detecting unit detect the longitudinal force, the transverse force, the vertical force and the displacement amount respectively. The acquisition device collects the longitudinal force, the transverse force, the vertical force and the displacement amount, and sends them to the computer. The computer analyzes the longitudinal force, the transverse force, the vertical force and the displacement amount to obtain the mechanical property of biological soft tissue.

In conclusion, in the mechanical property tester and testing method of biological soft tissue of the present invention, a fixture is provided for fixing the biological soft tissue, a transverse force applying device is provided for applying a force on the fixture, a vertical force applying device is provided such that shear deformation is caused in the biological soft tissue. And, the longitudinal force, the transverse force, the vertical force, and the amount of displacement are detected by the longitudinal pulling force detector, the transverse pulling force detector, the vertical pulling force detector and the displacement detecting unit respectively and analyzed. Thus, by means of the mechanical property tester and testing method of the invention, the shear test can be achieved in biological soft tissue, and the material response can be measured in complex shear mode.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A mechanical property tester of biological soft tissue, comprising:
    a base;
    a fixture disposed on the base for fixing the biological soft tissue;
    a transverse force applying device connected with the fixture for applying a transverse force on the fixture, the transverse force applying device comprising a transverse pulling force detector for detecting the transverse force applied on the fixture;
    a vertical force applying device connected with the fixture for applying a vertical force on the fixture, the vertical force applying device comprising a vertical pulling force detector for detecting the vertical force applied on the fixture;
    a longitudinal pulling force detector for holding the fixture and detecting a longitudinal force applied on the fixture,
    a displacement detecting unit disposed on the base for detecting the displacement of the fixture,
    an acquisition device for collecting the longitudinal force, the transverse force, the vertical force and the displacement; and
    a computer connected with the acquisition device, for analyzing the longitudinal force, the transverse force, the vertical force and the displacement,
    wherein the displacement detecting unit comprises a Y-axis displacement detector for detecting the displacement of the fixture in a longitudinal direction, an X-axis displacement detector for detecting the displacement of the fixture in a transverse direction, and a Z-axis displacement detector for detecting the displacement of the fixture in a vertical direction, and
    wherein a fixing frame is provided on the base for fixing the Y-axis displacement detector which is located above the fixture, the fixing frame comprising a fixing rod disposed vertically relative to the base, a mounting rod disposed vertically relative to the fixing rod and a fastener for fixing the mounting rod on the fixing rod, an elongated waist hole extending along the mounting rod being opened on the mounting rod, and the fastener extending through the elongated waist hole.

2. The mechanical property tester of biological soft tissue as claimed in claim 1, wherein the longitudinal pulling force detector comprises a plurality of clamping elements for clamping the fixture and multiple longitudinal pressure sub-detectors disposed correspondingly to the clamping elements, each of the longitudinal pressure sub-detectors detecting the longitudinal force of the fixture at the position of the corresponding clamping element.

3. The mechanical property tester of biological soft tissue as claimed in claim 2, wherein there are four clamping elements, the fixture being quadrangular, and the four clamping elements holding the four corners of the fixture respectively.

4. The mechanical property tester of biological soft tissue as claimed in claim 2, wherein each clamping element comprises an upper clamping board and a lower clamping board disposed oppositely and a connecting board for connecting the upper and lower clamping boards, a clamping chamber being enclosed by the upper clamping board, the lower clamping board and the connecting board, the fixture being C-shaped.

5. The mechanical property tester of biological soft tissue as claimed in claim 1, wherein the transverse force applying device also comprises a transverse traction wire for connecting the transverse pulling force detector with the fixture, the vertical force applying device also comprising a vertical traction wire for connecting the vertical pulling force detector with the fixture.

6. The mechanical property tester of biological soft tissue as claimed in claim 5, wherein the transverse force applying device also comprises a transverse driving device for driving the transverse traction wire, one end of the transverse pulling force detector being connected with the transverse traction wire, and the other end being connected with the transverse driving device, the vertical force applying device also comprising a vertical driving device for driving the vertical traction wire, one end of the vertical pulling force detector being connected with the vertical traction wire, and the other end being connected with the vertical driving device.

7. The mechanical property tester of biological soft tissue as claimed in claim 6, wherein the base is provided with a mounting base, and a first sliding base and a second sliding base which are fixed on the mounting base, the transverse pulling force detector being provided on the first sliding base, the vertical pulling force being provided on the second sliding base, the mounting base comprising a mounting part for fixing the fixture, a first extension plate and a second extension plate extending outwardly from the two adjacent lateral surfaces of the mounting part, the first extension plate being provided with a first rail extending along the extension direction of the transverse traction wire and cooperated with the first sliding base, the second extension plate being provided with a second rail extending along the extension direction of the vertical traction wire and cooperated with the second sliding base.

8. A mechanical property testing method of biological soft tissue comprising:
    providing the mechanical property tester of biological soft tissue of claim 1;
    fixing the biological soft tissue on the fixture of the mechanical property tester of biological soft tissue;
    applying a force on the fixture by the vertical force applying device and transverse force applying device, such that the fixture is displaced and the biological soft tissue is deformed; detecting the longitudinal force, the transverse force, the vertical force and the displacement mount by the longitudinal pulling force detector, the transverse force applying device, the vertical force applying device and the displacement detecting unit respectively;

collecting the longitudinal force, the transverse force, the vertical force and the displacement amount by the acquisition device; and analyzing the longitudinal force, the transverse force, the vertical force and the displacement amount collected by the acquisition device, to obtain the mechanical property of the biological soft tissue.

* * * * *